United States Patent [19]
Mahurkar

[11] Patent Number: 5,879,338
[45] Date of Patent: Mar. 9, 1999

[54] NEEDLE-SYRINGE ASSEMBLY FOR GUIDEWIRE INSERTION

[76] Inventor: Sakharam D. Mahurkar, 6171 N. Sheridan Rd., Suite 1112, Chicago, Ill. 60660

[21] Appl. No.: 618,624

[22] Filed: Mar. 19, 1996

Related U.S. Application Data

[63] Continuation-in-part of Ser. No. 587,030, Jan. 16, 1996, which is a continuation-in-part of Ser. No. 494,283, Jun. 23, 1995, Pat. No. 5,643,222, which is a continuation-in-part of Ser. No. 229,811, Apr. 19, 1994, Pat. No. 5,514,100, which is a division of Ser. No. 111,372, Aug. 23, 1993, Pat. No. 5,338,311, and a continuation-in-part of Ser. No. 573,663, Dec. 18, 1995, Pat. No. 5,685,862, which is a division of Ser. No. 229,811, Apr. 19, 1994, Pat. No. 5,514,100, which is a division of Ser. No. 111,372, Aug. 23, 1993, Pat. No. 5,338,311.

[51] Int. Cl.$^6$ .................................................. A61M 5/32
[52] U.S. Cl. ......................... 604/195; 604/164; 604/158; 226/127; 226/129
[58] Field of Search ...................................... 604/110, 158, 604/159, 161, 164–165, 167, 169, 170, 188, 181, 187, 194–198, 218, 239, 240–243, 236–238; 606/108; 600/433–435, 585, 573, 576, 578, 589; 226/127, 129, 130

[56] References Cited

U.S. PATENT DOCUMENTS

D. 298,352 11/1988 Raines .
2,888,923 6/1959 Cunha Reis .

(List continued on next page.)

FOREIGN PATENT DOCUMENTS

| 2004771 | 11/1969 | France . |
|---|---|---|
| 24 15 196 | 10/1975 | Germany . |
| 25 07 119 | 9/1976 | Germany . |
| 30 42 229 | 5/1982 | Germany . |

OTHER PUBLICATIONS

"Health Care" by Helene Cooper, Wall Street Journal (Nov. 25, 1992).
The G.M.P. Letter (May 1992).
Devices & Diagnostics Letter, vol. 19, No. 19 (May 8, 1992).
FDA Medical Bulletin, vol. 22, No. 2, (Sep. 22, 1992).
"Safer Syringes Boost Molder Opportunities" by Carl Kirkland, Plastic World, vol. 51/No. 8, pp. 20–24, (Aug. 1993).
"Untrasonics Get Medical Seal Of Approval" by Marcie Moskowitz, Plastic World, vol. 51/No. 8, pp. 26–28, (Aug. 1993).
Brochure for Arrow® Ravlerson Syringe.
Brochure for Syringes by Becton Dickinson of Franklin Lakes, New Jersey (1992).
Devices & Diagnostics Letter, p. 2 (Aug. 21, 1992).
Chiarello, Linda A., Reducing Needlestick Injuries among Health Care Workers: AIDS Clinical Care Oct. 1993, V.5 No. 10 Mass. Medical Society.

*Primary Examiner*—Ronald Stright
*Attorney, Agent, or Firm*—Arnold White & Durkee

[57] ABSTRACT

A needle-syringe for inserting a guidewire G in a patient comprises a barrel 10 and a hollow nozzle 15 opening into the interior of the barrel 10. It comprises a plunger 11 slidably mounted in the barrel 10 and a needle holder 14 slidably mounted in the longitudinal cavity of the plunger 11. A hollow guide member is mounted between the proximal ends of the needle holder 14 and the plunger 11 for guiding a guidewire G from the proximal end of the plunger 11 to the proximal end of the needle holder 14. The needle holder 14 includes a valve member for passing a guidewire G through the needle holder 14 while preventing blood from flowing between the interiors of the needle holder 14 and the hollow guide member. The guide member engages and retracts the needle holder 14 in response to relative rotational movement between the barrel 10 and the needle holder 14.

33 Claims, 10 Drawing Sheets

U.S. PATENT DOCUMENTS

| | | |
|---|---|---|
| 2,925,083 | 12/1957 | Craig . |
| 3,610,240 | 6/1967 | Harautuneian . |
| 3,658,061 | 4/1925 | Hall . |
| 4,068,659 | 1/1978 | Moorehead . |
| 4,233,982 | 11/1980 | Bauer et al. . |
| 4,245,635 | 1/1981 | Kontos . |
| 4,261,357 | 4/1981 | Kontos . |
| 4,274,408 | 6/1981 | Nimrod . |
| 4,417,886 | 11/1983 | Franhouser et al. . |
| 4,424,833 | 1/1984 | Spector et al. . |
| 4,425,120 | 1/1984 | Sampson et al. . |
| 4,468,224 | 8/1984 | Enzmann et al. . |
| 4,529,399 | 7/1985 | Groshong et al. . |
| 4,631,057 | 12/1986 | Mitchell . |
| 4,639,248 | 1/1987 | Schweblin . |
| 4,659,330 | 4/1987 | Nelson et al. . |
| 4,664,654 | 5/1987 | Strauss . |
| 4,666,435 | 5/1987 | Braginetz . |
| 4,693,708 | 9/1987 | Wanderer et al. . |
| 4,702,738 | 10/1987 | Spencer . |
| 4,710,170 | 12/1987 | Haber et al. . |
| 4,731,059 | 3/1988 | Wanderer et al. . |
| 4,731,068 | 3/1988 | Hesse . |
| 4,732,162 | 3/1988 | Martell . |
| 4,735,617 | 4/1988 | Nelson et al. . |
| 4,735,618 | 4/1988 | Hagen . |
| 4,742,910 | 5/1988 | Staebler . |
| 4,746,017 | 5/1988 | Howard et al. . |
| 4,747,831 | 5/1988 | Kulli . |
| 4,747,835 | 5/1988 | Sandhaus . |
| 4,747,836 | 5/1988 | Luther . |
| 4,752,290 | 6/1988 | Schramm . |
| 4,762,515 | 8/1988 | Luther et al. . |
| 4,762,516 | 8/1988 | Luther et al. . |
| 4,767,412 | 8/1988 | Hymanson . |
| 4,767,413 | 8/1988 | Haber et al. . |
| 4,778,453 | 10/1988 | Lopez . |
| 4,782,841 | 11/1988 | Lopez . |
| 4,790,822 | 12/1988 | Haining . |
| 4,799,926 | 1/1989 | Haber . |
| 4,801,295 | 1/1989 | Spencer . |
| 4,808,169 | 2/1989 | Haber et al. . |
| 4,813,426 | 3/1989 | Haber et al. . |
| 4,813,938 | 3/1989 | Raulerson . |
| 4,816,024 | 3/1989 | Sitar et al. . |
| 4,819,659 | 4/1989 | Sitar . |
| 4,826,488 | 5/1989 | Nelson et al. . |
| 4,826,489 | 5/1989 | Haber et al. . |
| 4,826,491 | 5/1989 | Schramm . |
| 4,828,107 | 5/1989 | Spencer . |
| 4,828,548 | 5/1989 | Walter . |
| 4,832,696 | 5/1989 | Luther et al. . |
| 4,834,717 | 5/1989 | Haber et al. . |
| 4,838,871 | 6/1989 | Luther . |
| 4,842,591 | 6/1989 | Luther . |
| 4,846,811 | 7/1989 | Vanderhoof . |
| 4,850,961 | 7/1989 | Wanderer et al. . |
| 4,850,976 | 6/1989 | Heinrich et al. . |
| 4,852,584 | 8/1989 | Selby . |
| 4,860,742 | 8/1989 | Park et al. ............................. 606/108 |
| 4,863,435 | 9/1989 | Sturman et al. . |
| 4,863,436 | 9/1989 | Glick . |
| 4,869,717 | 9/1989 | Adair . |
| 4,872,552 | 10/1989 | Unger . |
| 4,874,383 | 10/1989 | McNaughton . |
| 4,874,384 | 10/1989 | Nunez . |
| 4,883,469 | 11/1989 | Glazier . |
| 4,887,998 | 12/1989 | Martin et al. . |
| 4,892,525 | 1/1990 | Hermann, Jr. et al. . |
| 4,894,054 | 1/1990 | Miskinyar . |
| 4,894,055 | 1/1990 | Sudnak . |
| 4,897,083 | 1/1990 | Martell . |
| 4,898,588 | 2/1990 | Roberts . |
| 4,900,311 | 2/1990 | Stern et al. . |
| 4,903,832 | 2/1990 | Stewart . |
| 4,906,235 | 3/1990 | Roberts . |
| 4,909,794 | 3/1990 | Haber et al. . |
| 4,911,693 | 3/1990 | Paris . |
| 4,915,696 | 4/1990 | Feimer . |
| 4,915,697 | 4/1990 | DuPont . |
| 4,917,673 | 4/1990 | Coplin . |
| 4,919,656 | 4/1990 | Bracker et al. . |
| 4,921,489 | 5/1990 | Frizzell . |
| 4,927,019 | 5/1990 | Haber et al. . |
| 4,927,417 | 5/1990 | Moncada et al. . |
| 4,928,824 | 5/1990 | Barasch . |
| 4,929,241 | 5/1990 | Kulli . |
| 4,931,040 | 6/1990 | Haber et al. . |
| 4,931,048 | 6/1990 | Lopez . |
| 4,932,940 | 6/1990 | Walker et al. . |
| 4,932,946 | 6/1990 | Shields . |
| 4,935,013 | 6/1990 | Haber et al. . |
| 4,935,015 | 6/1990 | Hall . |
| 4,944,723 | 7/1990 | Haber et al. . |
| 4,944,728 | 7/1990 | Carrell et al. . |
| 4,944,731 | 7/1990 | Cole . |
| 4,946,447 | 8/1990 | Harcastle et al. . |
| 4,950,241 | 8/1990 | Ranford . |
| 4,950,251 | 8/1990 | Haining . |
| 4,950,252 | 8/1990 | Luther et al. . |
| 4,958,622 | 9/1990 | Selenke . |
| 4,964,854 | 10/1990 | Luther . |
| 4,973,316 | 11/1990 | Dysarz . |
| 4,976,702 | 12/1990 | Andrews et al. . |
| 4,986,813 | 1/1991 | Blake, III et al. . |
| 4,986,819 | 1/1991 | Sobel . |
| 4,988,339 | 1/1991 | Vadher . |
| 4,994,034 | 2/1991 | Botich et al. . |
| 4,994,042 | 2/1991 | Vadher . |
| 4,994,044 | 2/1991 | LoDuca . |
| 4,997,422 | 3/1991 | Chow et al. . |
| 4,998,922 | 3/1991 | Kuracina et al. . |
| 5,000,167 | 3/1991 | Sunderland . |
| 5,002,536 | 3/1991 | Thompson et al. . |
| 5,013,304 | 5/1991 | Russell et al. . |
| 5,015,241 | 5/1991 | Feimer . |
| 5,019,045 | 5/1991 | Lee . |
| 5,019,051 | 5/1991 | Hake . |
| 5,024,326 | 6/1991 | Sandel et al. . |
| 5,024,660 | 6/1991 | McNaughton . |
| 5,026,345 | 6/1991 | Teringo . |
| 5,026,354 | 6/1991 | Kocses . |
| 5,030,209 | 7/1991 | Wanderer et al. . |
| 5,030,212 | 7/1991 | Rose . |
| 5,037,400 | 8/1991 | Curry . |
| 5,037,401 | 8/1991 | DeCamp . |
| 5,045,062 | 9/1991 | Henson . |
| 5,046,508 | 9/1991 | Weissler . |
| 5,049,136 | 9/1991 | Johnson . |
| 5,051,109 | 9/1991 | Simon . |
| 5,053,017 | 10/1991 | Chamuel . |
| 5,057,088 | 10/1991 | Narayanan et al. . |
| 5,057,089 | 10/1991 | Greco . |
| 5,059,180 | 10/1991 | McLees . |
| 5,061,249 | 10/1991 | Campbell . |
| 5,066,279 | 11/1991 | Russell . |
| 5,066,281 | 11/1991 | Stevenson-Michener . |
| 5,067,942 | 11/1991 | Jaffe et al. . |
| 5,067,944 | 11/1991 | Nichols . |
| 5,067,946 | 11/1991 | Zhadanov . |
| 5,067,949 | 11/1991 | Freundlich et al. . |
| 5,069,669 | 12/1991 | Kole . |

| | | | | | |
|---|---|---|---|---|---|
| 5,078,693 | 1/1992 | Shine . | 5,219,333 | 6/1993 | Sagstetter et al. . |
| 5,084,019 | 1/1992 | Gartz . | 5,219,338 | 6/1993 | Haworth . |
| 5,086,780 | 2/1992 | Schmitt . | 5,221,262 | 6/1993 | Kite . |
| 5,088,987 | 2/1992 | Noonan, Jr. . | 5,222,942 | 6/1993 | Bader . |
| 5,088,988 | 2/1992 | Talonn et al. . | 5,222,943 | 6/1993 | Mazzara . |
| 5,092,853 | 3/1992 | Couvertier, II . | 5,222,944 | 6/1993 | Harris . |
| 5,098,394 | 3/1992 | Luther . | 5,222,945 | 6/1993 | Basdnight . |
| 5,098,402 | 3/1992 | Davis . | 5,222,947 | 6/1993 | D'Amico . |
| 5,106,379 | 4/1992 | Leap . | 5,226,893 | 7/1993 | Kayser . |
| 5,106,380 | 4/1992 | Lobello . | 5,232,456 | 8/1993 | Gonzalez . |
| 5,108,378 | 4/1992 | Firth et al. . | 5,242,400 | 9/1993 | Blake, III et al. . |
| 5,112,307 | 5/1992 | Haber et al. . | 5,246,428 | 9/1993 | Falknor . |
| 5,112,315 | 5/1992 | Gloyer et al. . | 5,250,031 | 10/1993 | Kaplan et al. . |
| 5,114,404 | 5/1992 | Paxton et al. . | 5,254,099 | 10/1993 | Kuracina et al. . |
| 5,116,325 | 5/1992 | Paterson . | 5,261,894 | 11/1993 | Smith et al. . |
| 5,120,309 | 6/1992 | Watts . | 5,267,961 | 12/1993 | Shaw . |
| 5,122,118 | 6/1992 | Haber et al. . | 5,267,973 | 12/1993 | Haber et al. . |
| 5,125,898 | 6/1992 | Kaufhold, Jr. et al. . | 5,267,976 | 12/1993 | Guerineau et al. . |
| 5,127,910 | 7/1992 | Talonn et al. . | 5,269,765 | 12/1993 | Kuracina . |
| 5,135,504 | 8/1992 | McLees . | 5,273,538 | 12/1993 | Chen . |
| 5,135,505 | 8/1992 | Kaufman . | 5,273,539 | 12/1993 | Chen . |
| 5,147,324 | 9/1992 | Skakoon et al. . | 5,273,541 | 12/1993 | Malenchek . |
| 5,147,326 | 9/1992 | Talonn et al. . | 5,273,543 | 12/1993 | Bell et al. . |
| 5,152,750 | 10/1992 | Haining . | 5,279,582 | 1/1994 | Davison et al. . |
| 5,156,598 | 10/1992 | Skakoon et al. . | 5,290,233 | 3/1994 | Campbell . |
| 5,160,326 | 11/1992 | Talonn et al. . | 5,295,975 | 3/1994 | Lockwood, Jr. . |
| 5,163,908 | 11/1992 | Lambert . | 5,300,030 | 4/1994 | Crossman et al. . |
| 5,163,917 | 11/1992 | Huefner et al. . | 5,300,039 | 4/1994 | Poulsen . |
| 5,171,300 | 12/1992 | Blake, III et al. . | 5,304,137 | 4/1994 | Fluke . |
| 5,171,303 | 12/1992 | DeCamp . | 5,304,149 | 4/1994 | Morigi . |
| 5,176,640 | 1/1993 | Nacci et al. . | 5,304,150 | 4/1994 | Duplan et al. . |
| 5,176,655 | 1/1993 | McCormick et al. . | 5,304,154 | 4/1994 | Gloyer et al. . |
| 5,181,524 | 1/1993 | Wanderer et al. . | 5,312,347 | 5/1994 | Osborne et al. . |
| 5,183,468 | 2/1993 | McLees . | 5,312,365 | 5/1994 | Firth et al. . |
| 5,188,119 | 2/1993 | Sunderland . | 5,318,536 | 6/1994 | Williams . |
| 5,188,611 | 2/1993 | Orgain . | 5,320,606 | 6/1994 | Jore . |
| 5,188,613 | 2/1993 | Shaw . | 5,324,265 | 6/1994 | Murray et al. . |
| 5,190,526 | 3/1993 | Murray et al. . | 5,336,186 | 8/1994 | Haber et al. . |
| 5,190,532 | 3/1993 | Yu . | 5,336,187 | 8/1994 | Terry et al. . |
| 5,195,973 | 3/1993 | Novick . | 5,336,197 | 8/1994 | Kuracina et al. . |
| 5,195,975 | 3/1993 | Castagna . | 5,336,198 | 8/1994 | Silver et al. . |
| 5,195,982 | 3/1993 | Hoenig . | 5,338,304 | 8/1994 | Adams . |
| 5,195,983 | 3/1993 | Boese . | 5,342,323 | 8/1994 | Haining . |
| 5,195,992 | 3/1993 | Dudar et al. . | 5,344,403 | 9/1994 | Lee . |
| 5,195,993 | 3/1993 | Gianakos . | 5,352,208 | 10/1994 | Robinson . |
| 5,197,953 | 3/1993 | Colonna . | 5,360,408 | 11/1994 | Vaillancourt . |
| 5,197,954 | 3/1993 | Cameron . | 5,364,359 | 11/1994 | Van den Haak . |
| 5,201,718 | 4/1993 | Whisson . | 5,376,080 | 12/1994 | Petrussa . |
| 5,205,823 | 4/1993 | Zdeb . | 5,378,240 | 1/1995 | Curie et al. . |
| 5,209,739 | 5/1993 | Talalay . | 5,380,297 | 1/1995 | Wadman et al. . |
| 5,211,629 | 5/1993 | Pressly et al. . | 5,385,555 | 1/1995 | Hausser . |
| 5,215,524 | 6/1993 | Vallelunga et al. . | 5,393,301 | 2/1995 | Goldberg . |
| 5,215,525 | 6/1993 | Sturman . | 5,395,337 | 3/1995 | Clemens et al. . |
| 5,215,528 | 6/1993 | Purdy et al. . | 5,399,170 | 3/1995 | Whitley . |
| 5,215,529 | 6/1993 | Fields et al. . | 5,403,286 | 4/1995 | Lockwood, Jr. . |
| 5,215,533 | 6/1993 | Robb . | 5,403,431 | 4/1995 | Botich et al. . |
| 5,215,534 | 6/1993 | DeHarde et al. . | 5,407,436 | 4/1995 | Toft et al. . |
| 5,215,535 | 6/1993 | Gettig et al. . | 5,415,645 | 5/1995 | Friend et al. . |
| 5,217,436 | 6/1993 | Farkas . | 5,419,773 | 5/1995 | Rupp . |
| 5,217,437 | 6/1993 | Talonn et al. . | | | |

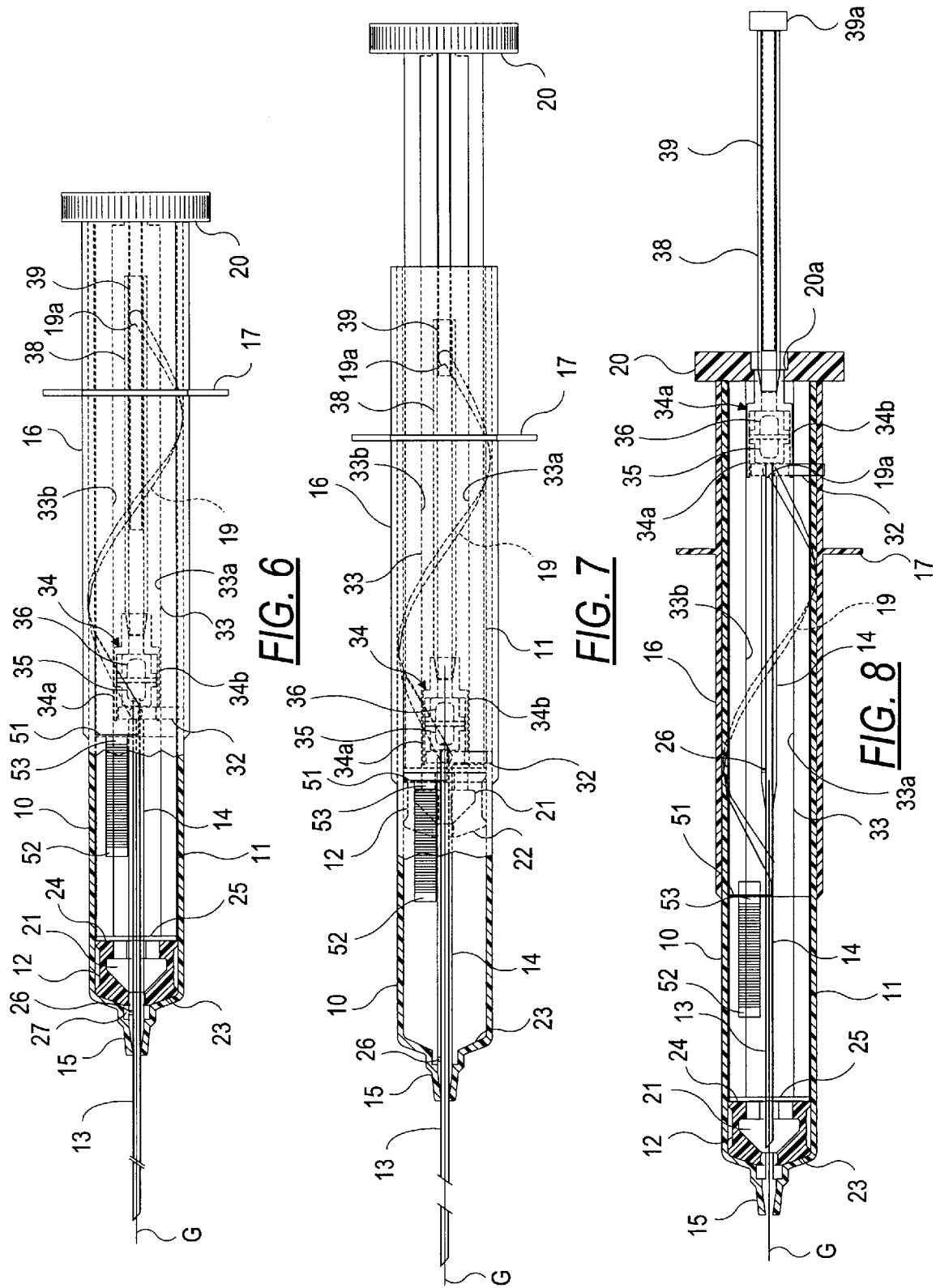

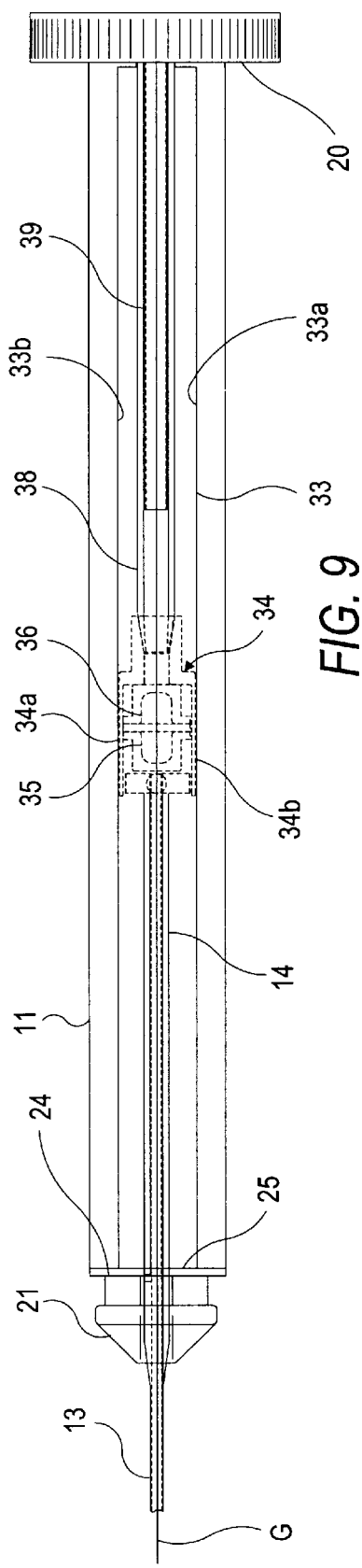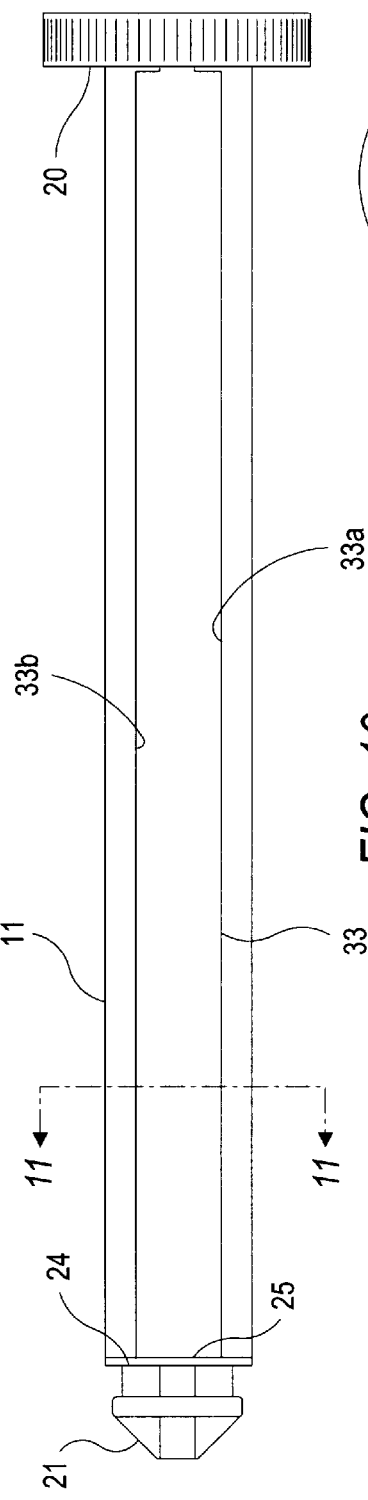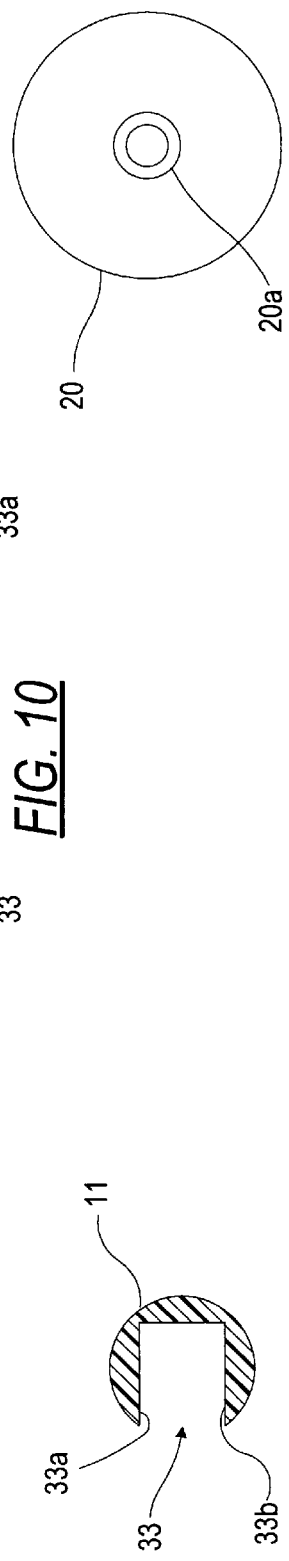
FIG. 9
FIG. 10
FIG. 11
FIG. 12

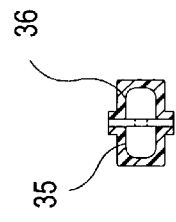
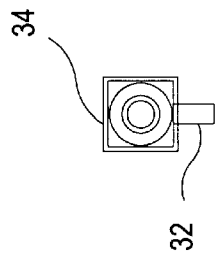
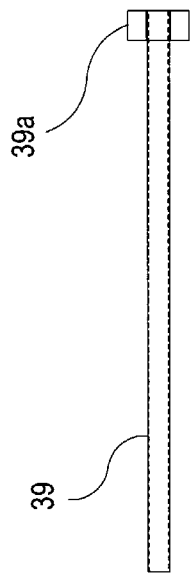
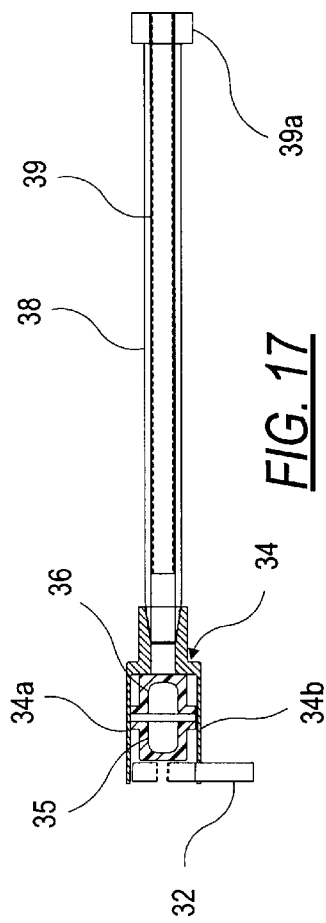
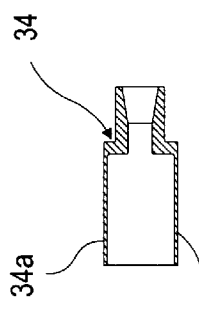
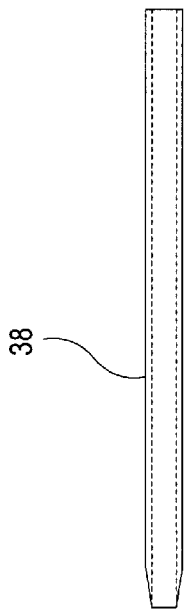

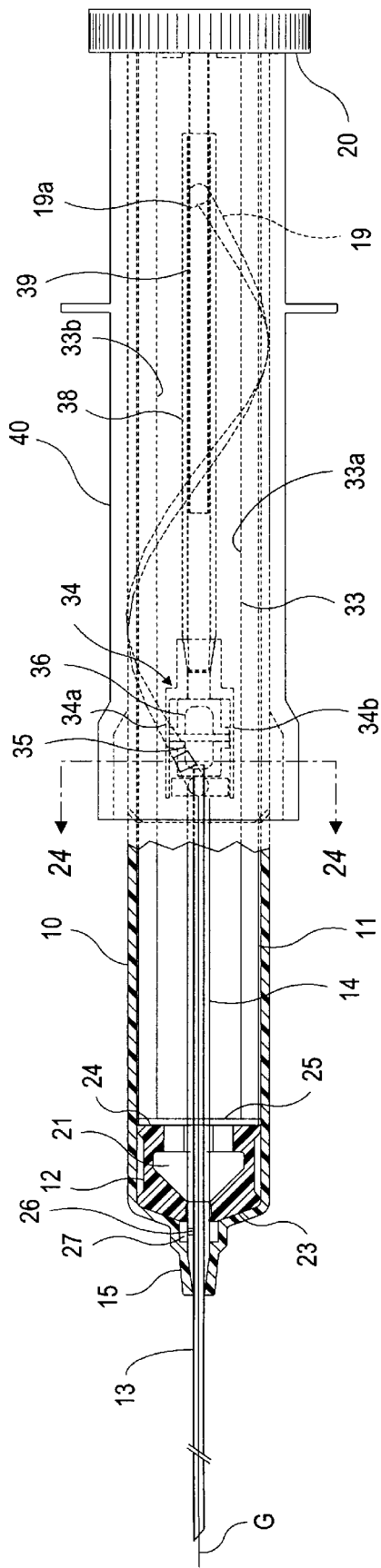
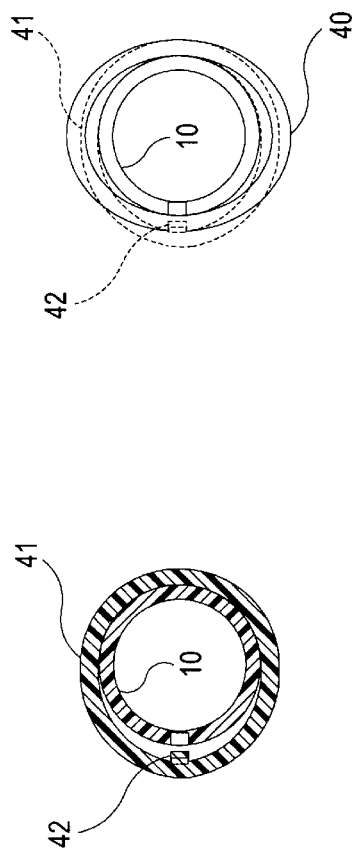
FIG. 23
FIG. 25
FIG. 24

NEEDLE-SYRINGE ASSEMBLY FOR GUIDEWIRE INSERTION

CROSS-REFERENCES TO RELATED APPLICATIONS

This application is a continuation-in-part of Ser. No. 08/587,030, filed Jan. 16, 1996, now allowed, which is a continuation-in-part of Ser. No. 08/494,283, filed Jun. 23, 1995, now U.S. Pat. No. 5,643,222, which is a continuation-in-part of Ser. No. 08/229,811, filed Apr. 19, 1994, now U.S. Pat. No. 5,514,100, which is a divisional of Ser. No. 08/111,372, filed Aug. 23, 1993, now U.S. Pat. No. 5,338,311. this application is also a continuation-in-part of Ser. No. 08/573,663, filed Dec. 18, 1995, now U.S. Pat. No. 5,685,862, which is a divisional of Ser. No. 08/229,811, filed Apr. 19, 1994, now U.S. Pat. No. 5,514,100, which is a divisional of Ser. No. 08/111,372, filed Aug. 23, 1993, now U.S. Pat. No. 5,338,311.

FIELD OF THE INVENTION

The present invention generally relates to hypodermic needle syringe devices for use in the insertion of guidewires into patients. In particular, the present invention relates to such a needle-syringe assembly which conceals the sharp point of the hypodermic needle following insertion of the guidewire.

BACKGROUND OF THE INVENTION

A hypodermic needle has many applications in modern medicine. One application is to fit the hypodermic needle onto a syringe and to then insert the needle into a person's body for intramuscular, subcutaneous, or intravenous injection of medications. A hypodermic needle entering into a patient's body is invariably contaminated by the patient's blood and body fluids. Following use of the needle, the needle presents a risk to physicians, nurses, and other health care personnel because the needle might transmit an infection or disease to such personnel if it were to accidentally puncture them. Thus, health care personnel are in constant danger of contracting infections and diseases, some of which may be deadly. Other potential victims of accidental needle punctures include sanitation workers which later dispose of garbage containing the hypodermic needle. The diseases which may be transmitted by a contaminated hypodermic needle include Immune Deficiency Virus, Hepatitis, Rabies, Kure, Encephalitis, and Arbor viruses. The outcome of contracting one of these diseases is often fatal because there are no known cures for any of these diseases. Often a needle puncture in a person's skin is so trivial that it remains unrecognized until the person becomes seriously ill.

The problem of suffering accidental needle punctures is well recognized. As a result, enormous inventive effort has been devoted to concealing the sharp needle point of hypodermic needles.

The deep-seated central veins, such as subclavian, jugular and femoral veins as well as arteries can only be accessed by negotiating a guidewire, through the puncturing needle, after disconnecting the syringe. The blood gushing out from the needle interferes with the visibility and insertion of the guidewire inside the needle. The blood also contaminates the area of operation and makes the blind insertion procedure even more difficult. The risks of needle stick are further multiplied by free sharp objects, scattered in a limited field. The present invention permits the insertion of the guidewire through the plunger itself without removing the syringe from the needle, as well as making the procedure essentially bloodless. It also avoids the needle puncture by retracting the needle even before it comes out of the patient's body.

SUMMARY OF THE INVENTION

A primary object of the present invention is to improve the needle-syringe-guidewire assembly described in the aforementioned U.S. Pat. No. 5,338,311 and patent application.

One specific object of this invention is to provide an improved needle-syringe-guidewire assembly which provides good structural stability for the mechanism that is used to insert the guidewire and subsequently retract the needle after it has been used.

Yet another object of the present invention is to provide such an improved needle-syringe-guidewire assembly which facilitates fabrication, and reduces the cost, of the assembly.

Still another object of the present invention is to provide such an improved needle-syringe-guidewire assembly which facilitates the operation of the assembly, particularly when it is desired to retract the needle prior to disposing of the needle-syringe assembly.

Another object of the present invention is to provide such an improved needle-syringe assembly which improves the acceptability of the assembly by providing an external appearance which is virtually the same as that of conventional hypodermic needle assemblies which do not provide for needle retraction.

A further object of the invention is to provide such an improved needle-syringe assembly that may have the same number of components as the combination syringe and a guidewire introducer needle with a valve and side port, and also provides needle retraction as an added safety feature.

Other objects and advantages of the invention will become apparent upon reading the following detailed description and upon reference to the accompanying drawings.

In accordance with the present invention, the foregoing objectives are realized by providing a needle-syringe assembly, operable in a normal mode and convertible to a retraction mode, comprising an elongated, generally cylindrical barrel forming a hollow nozzle located at the distal end of the barrel and opening into the interior of the barrel; a plunger slidably mounted in the barrel and forming a longitudinal cavity extending between the distal end and the proximal end of the plunger; a needle holder slidably mounted in the longitudinal cavity of the plunger; hollow guide means mounted between the proximal ends of the needle holder and the plunger for guiding a guidewire from the proximal ends of the plunger to the proximal end of the needle holder, the needle holder including valve means for passing a guidewire therethrough while preventing blood from flowing between the interiors of the needle holder and the hollow guide means, the guide means forming a spiral channel extending along a proximal end portion of the barrel for retracting the needle holder within the barrel in response to relative rotational movement between the barrel and the plunger; and latching means on the barrel for latching and unlatching the needle holder at the distal end of the spiral channel.

BRIEF DESCRIPTION OF THE DRAWINGS

FIG. 6 is a reduced side elevation, partially in section, of the assembly shown in FIG. 5;

FIG. 7 is the same view shown in FIG. 6, but with the plunger partially retracted;

FIG. 8 is the same view shown in FIG. 6 with the needle holder in the retracted position and the plunger in its fully advanced position;

FIG. 9 is an enlarged side elevation of the plunger and needle holder in the assembly of FIGS. 1–8;

FIG. 10 is an enlarged side elevation of the plunger in the assembly of FIGS. 1–8;

FIG. 11 is a section taken generally along line 11—11 in FIG. 10;

FIG. 12 is an end elevation of the plunger of FIG. 10;

FIG. 17 is a longitudinal section of the valve assembly attached to the needle holder in the assembly of FIGS. 1–8, and a side elevation of the guide tubes attached to the valve assembly;

FIG. 18 is a separate longitudinal section of the valve elements of FIG. 17;

FIG. 19 is a separate longitudinal section of the valve housing of FIG. 17;

FIG. 20 is an end elevation of the housing of FIG. 19

FIG. 21 is a separate side elevation of the outer guide tube shown in FIG. 17;

FIG. 22 is a separate side elevation of the inner guide tube of FIG. 17;

FIG. 23 is a side elevation, partially in section, of a modified needle-syringe-guidewire assembly embodying the present invention;

FIG. 24 is a section taken generally along lines 24—24 in FIG. 23;

FIG. 25 is a cross-sectional view similar to FIG. 24 but illustrating the external sleeve in two different positions, and with the cross-sectional hatching removed for clarity.

DETAILED DESCRIPTION OF THE PREFERRED EMBODIMENTS

Figure 1:
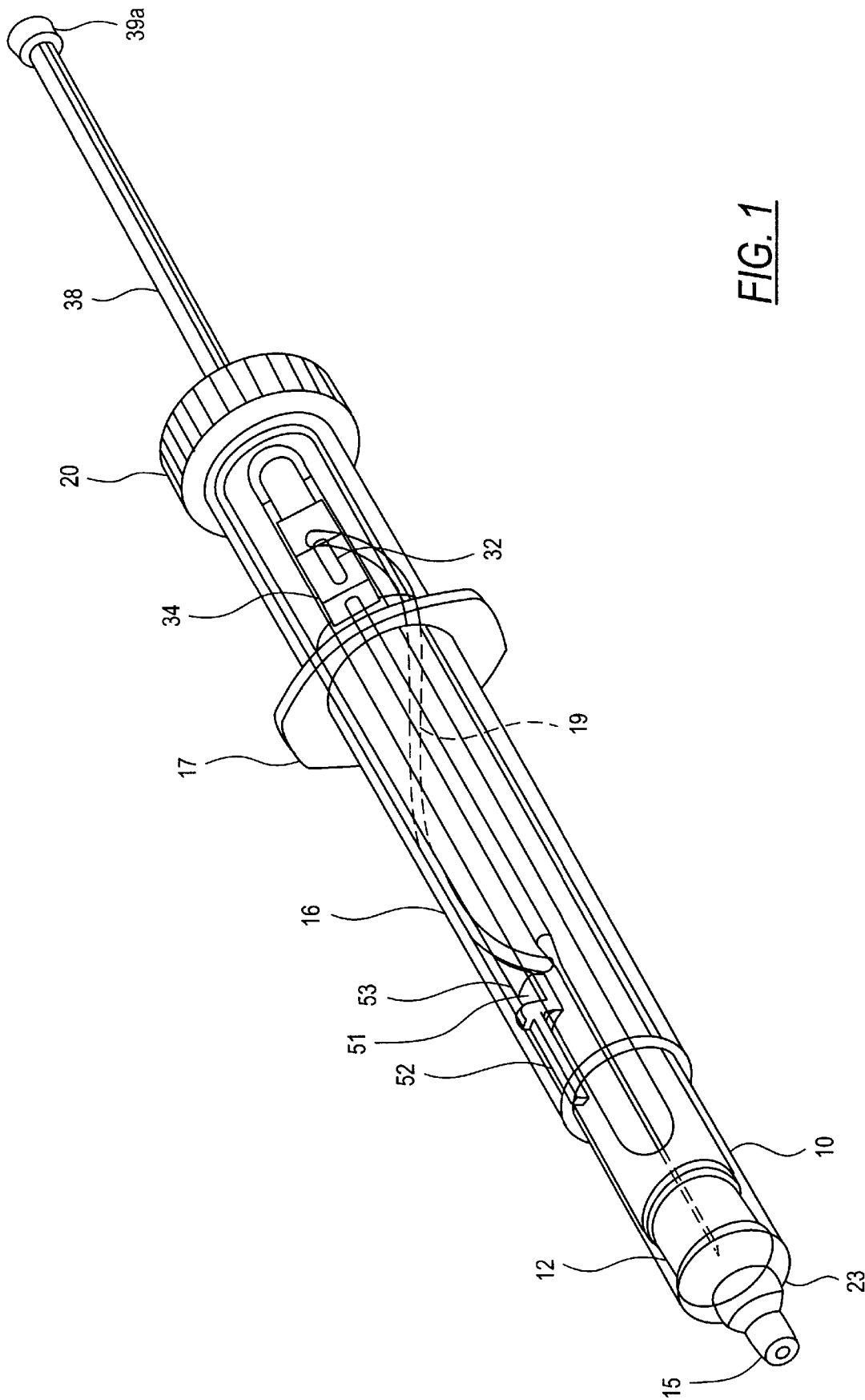
FIG. 1 is a perspective view of a needle-syring-guidewire assembly embodying the present invention with the needle fully retracted.
Figure 2:
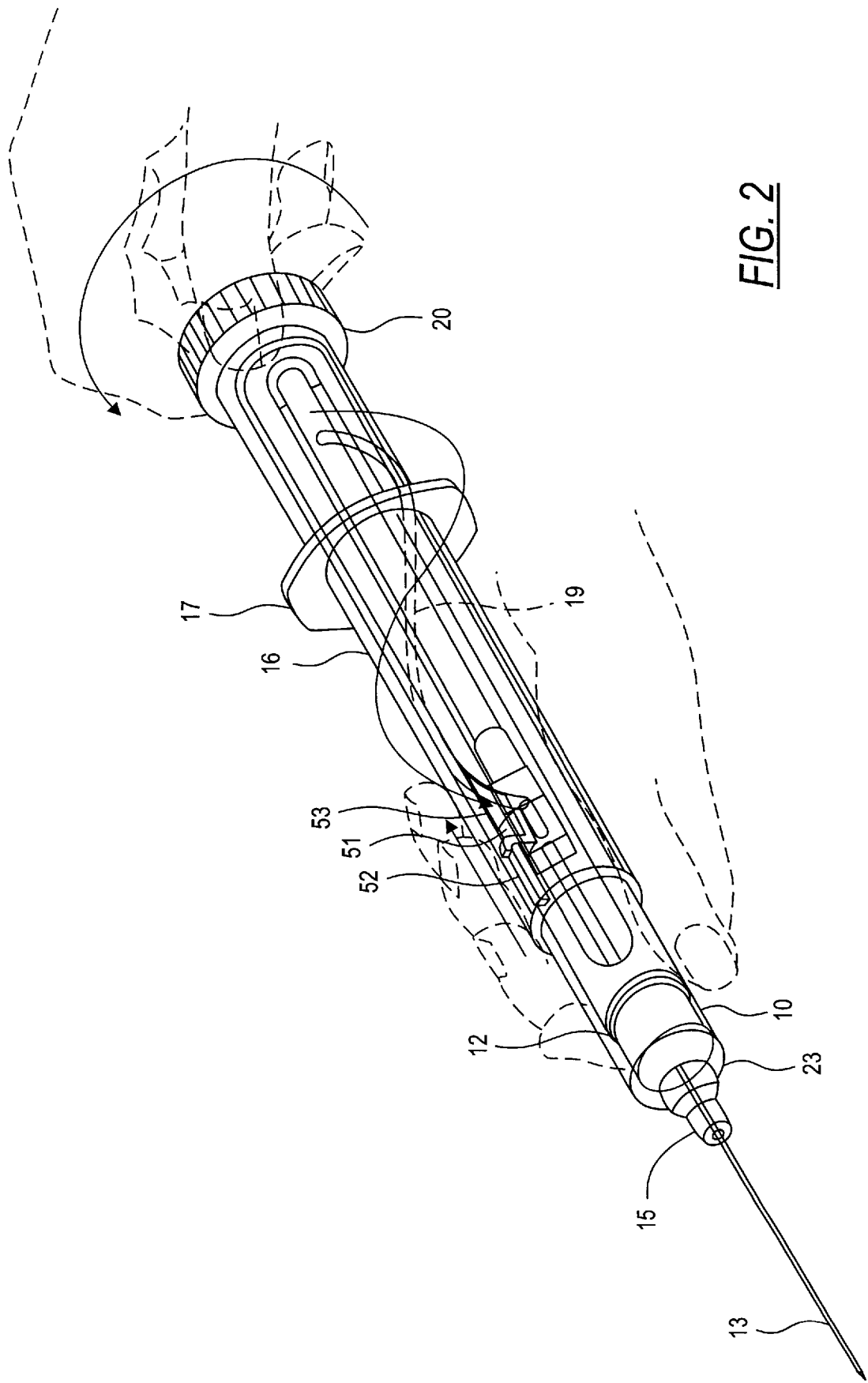
FIG. 2 is a reduced perspective view of the same assembly shown in FIG. 1, with the needle in its advanced position.
Figure 3:
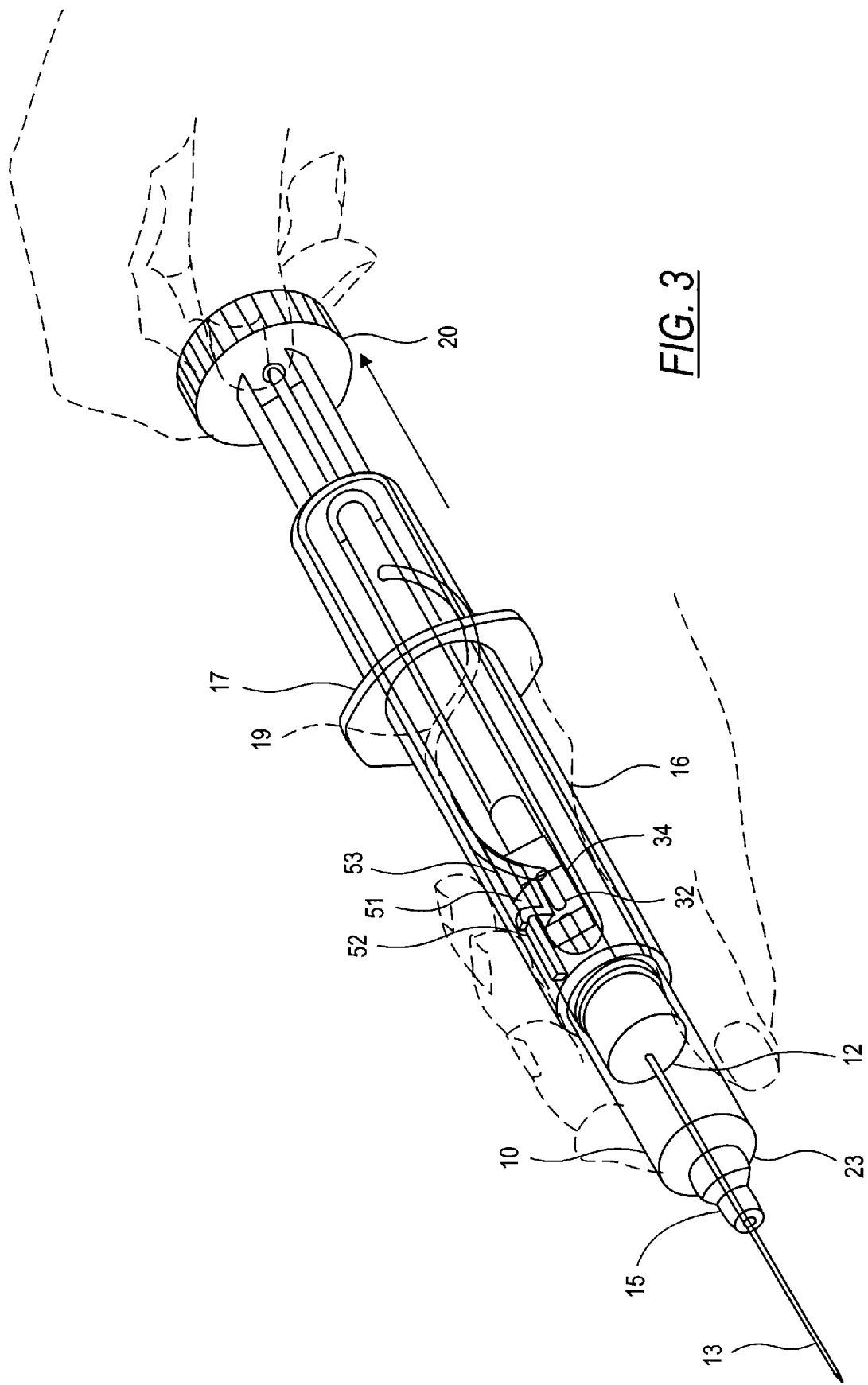
FIG. 3 is a reduced perspective view of the same assembly shown in FIG. 1, with the needle in its advanced position and the plunger partially retracted.
Figure 4:
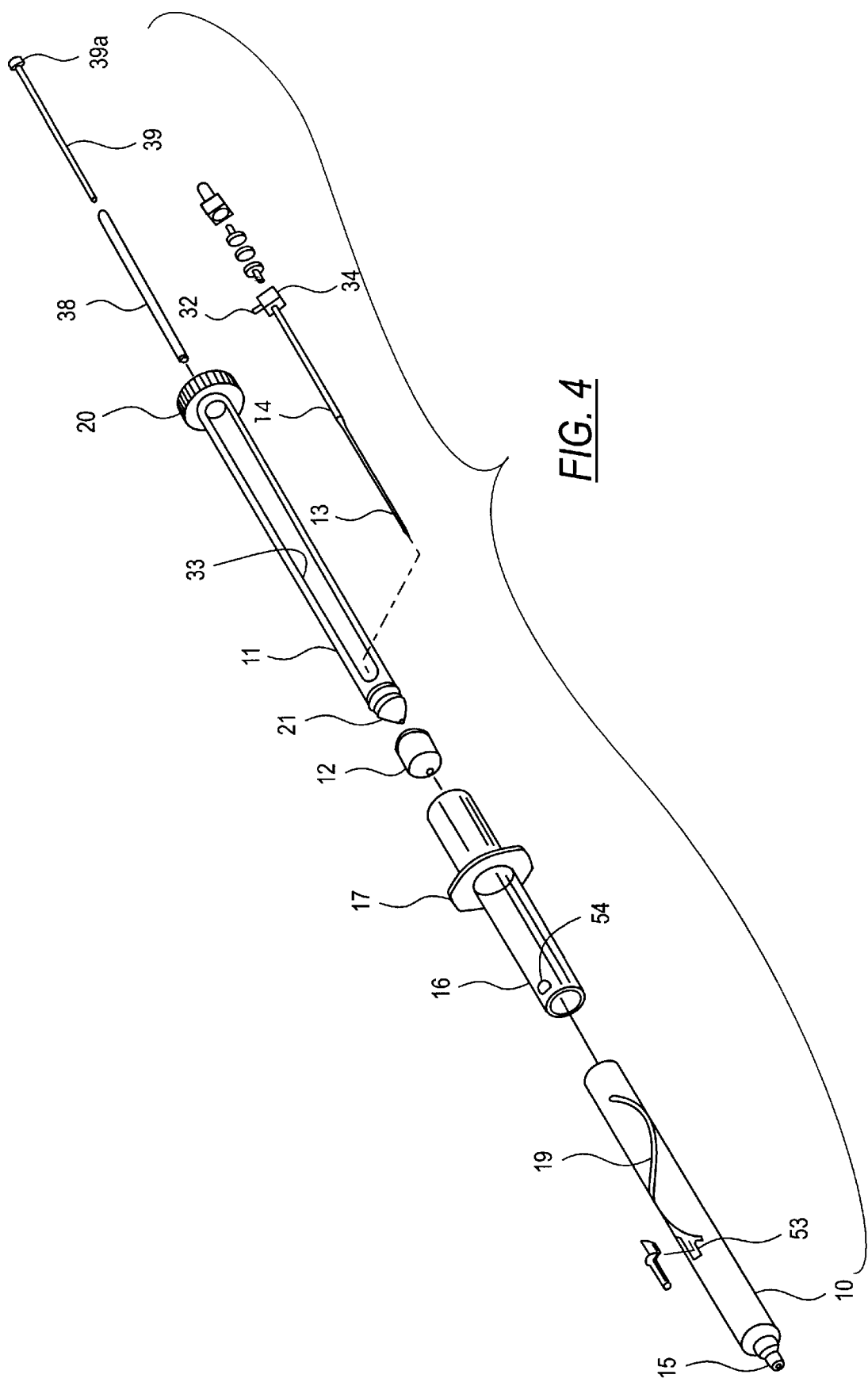
FIG. 4 is an exploded perspective of the needle-syringe-guidewire assembly of FIG. 1–3.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

In order to satisfy the best mode requirement for this disclosure, several different modes of the invention, each with its own unique features and alternate embodiments, are described. Permutations and combinations of these features will, however, lead to further modes.

Turning now to the drawings, FIGS. 1–22 illustrate a needle-syringe guidewire assembly including a barrel 10, a plunger 11, a hollow plunger cap 12, a hypodermic needle 13, and a needle holder 14. This assembly is used to puncture a patient's vein or artery and then insert a guidewire G through the puncture. The barrel 10 is a hollow cylinder which terminates in a hollow tapered nozzle 15 at the distal end thereof. The interior of the nozzle 15 communicates with the hollow interior of the tubular body portion of the barrel 10. The proximal portion of the barrel is telescoped within, and bonded to, a sleeve 16. An outwardly extending flange 17 near the proximal end of the sleeve 16 facilitates gripping of the syringe with the user's fingers when it is desired to move the plunger 11 relative to the barrel 10.

The proximal end portion of the barrel 10 within the sleeve 16 forms a spiral slot 19 within its wall. As will be described below, this spiral slot 19 provides an internal retraction track for the needle holder 14 and the hypodermic needle 13. The spiral slot 19 extends along a sufficient length to accommodate retraction of the needle holder 14 through a distance that is sufficient to draw the entire length of the needle 13 inside the barrel 10, as described in more detail below. The outer surface of the barrel 10 preferably contains graduations (not shown) indicating the volume level of fluid in the barrel. These graduations take into account the volume of the internal components such as the needle holder 14.

The proximal end of the plunger 11 forms a knob 20 that can be grasped by a user to effect linear or rotary movement of the plunger 11 relative to the barrel 10. The periphery of the knob 20 is serrated to facilitate gripping of the knob for rotary movements of the plunger. The distal end of the plunger 11 forms a head 21 to accommodate the hollow rubber plunger cap 12. The outside diameter of the resilient cap 12 is reduced in the central portion so that the cap engages the inside wall of the barrel 10 only at the pliable margins of the ends of the cap. The diameter of the engaging end portions of the cap 12 is slightly larger than the inside diameter of the barrel 10 so that the cap presses firmly against the inside wall of the barrel to form an air-tight and liquid-tight seal at the cap/barrel interface. The inner margins of the cap 12 make a similar tight contact with the outer surface of the needle holder 14. The distal end 22 of the cap 12 is conical to conform to the conical distal end 23 of the inside surface of the barrel 10 when the plunger 11 is fully advanced within the barrel.

The head 21 of the plunger 11 is configured to fit tightly within the hollow plunger cap 12. With the cap 12 locked onto the head 21 of the plunger, the flat proximal end 24 of the cap abuts the flat surface of a circular disc 25 at the base of the plunger head 21. Due to the air-tight and liquid-tight seal between the plunger cap 12 and the barrel 10, as well as the needle holder 14, advancing movement of the plunger 11 inside the barrel 10 creates pressure in the interior of the barrel between the plunger cap and the distal end of the barrel. Similarly, retracting movement of the plunger 11 creates a vacuum in that portion of the barrel interior.

The hypodermic needle 13 projects from the distal end of the elongated needle holder 14, which is detachably interlocked to the barrel 10. Prior to use of the needle-syringe assembly, the needle 13 is covered by a protective cap (not shown) which prevents needle pricks and preserves sterility prior to use. Both the needle 13 and the needle holder 14 are hollow, and the interior of the hollow needle 13 communicates with the interior of the barrel 10 through an aperture 26 in the side walls of the needle 13 and the needle holder 14 (FIGS. 5–8). Prior to and during use of the needle-syringe assembly for withdrawal of blood and insertion of the guidewire (hereafter referred to as "normal use"), the aperture 26 is positioned at the base of the barrel nozzle 15 (FIG. 5), within a small cylindrical cavity 27. The aperture 26 permits blood to enter or exit from the barrel 10 via the needle 13 and the needle holder 14.

During normal use of the needle-syringe assembly, the needle holder 14 is locked to the barrel 10, and the plunger 11 and its cap 12 are free to slide longitudinally back and forth along the needle holder. The needle holder 14 includes a lateral arm 32 extending radially across the barrel 10 at the proximal end of the holder 14.

To permit relative sliding movement between the plunger 11 and the needle holder 14 in the longitudinal direction, the needle holder is mounted in a longitudinal channel 33 formed as an integral part of the plunger 11. The proximal end of the needle holder 14 terminates in a small rectangular housing 34 that slides on the bottom wall of the channel 33. The parallel side walls 34a and 34b of the housing slide on the opposed side walls 33a and 33b of the channel 33. The three pairs of engaging walls stabilize the needle holder 14 as it slides longitudinally back and forth within the plunger channel 33, and also constrain the lateral arm 32 of the needle holder against any angular or rotational displacement relative to the plunger 11. That is, the plunger 11 and the needle holder 14 can rotate only in unison with each other, although they are free to move independently of each other in the longitudinal direction.

To lock the needle holder 14 to the barrel 10, the outer surface of the distal end portion of the needle holder is tapered to mate with a complementary tapered surface on the inside wall of the barrel nozzle 15. These tapered surfaces are conventionally known as locking luer tapers, and the angle of the taper (typically 6% of the diameter) is conventionally known as a locking taper angle. In a preferred embodiment, the taper has a length between about 0.185 and about 0.250 inch with a diameter of 0.094 inch at one end and a diameter of 0.082 inch at the other end.

The locking tapered surfaces are engaged during assembly of the needle syringe, when the plunger 11 and needle holder 14 are inserted into the barrel 10 through the open proximal end of the barrel. The resultant locking luer taper can be released only by the application of simultaneous axial and rotational forces.

The proximal end of the needle holder 14 is also locked to the barrel 10, via the lateral arm 32. This arm 32, which is formed as an integral part of the housing 34, extends radially beyond the plunger and fits into the spiral slot 19 in the barrel 10. The arm 32 can be locked to the barrel 10 at either end of the spiral slot 19 and, when so locked, permits only reciprocal linear movement of the plunger 11, to create vacuum to withdraw blood and pressure to return blood to the patient via the hypodermic needle. When the arm 32 is locked at either end of the slot 19, the plunger 11 cannot be rotated within the barrel 10.

The housing 34 contains a pair of dome valves 35 and 36 which permit the guidewire G to pass through the housing 34 and into the needle holder 14 while preventing blood from flowing proximally from the hollow interior of the needle 13. The two dome valves 35 and 36 face in opposite directions so that one valve prevents blood flow when the plunger is drawing a vacuum in the barrel, and the other valve prevents blood flow when the plunger is producing a positive pressure in the barrel. These valves are sufficiently flexible that finger pressure on the guidewire G is sufficient to cause the guidewire to pass through each valve.

To facilitate entry of the guidewire G into the housing 34 and the valves 35 and 36 therein, the proximal end of the housing 34 may form a tapered entry throat to guide the tip of the guidewire toward the slit in the center of the valve 36. The proximal end of the housing 34 receives, and is attached to, the distal end of a guide tube 38 which telescopes over a smaller guide tube 39. The smaller guide tube 39, which has an inside diameter only slightly larger than the diameter of the guidewire G, extends through a hole in the center of the knob 20 on the proximal end of the plunger 11. A head 39a on the end of the tube 39 nests in a recess 20a in the proximal surface of the knob 20 so that the proximal end of the tube cannot move beyond the knob 20 in a distal direction. This feature limits the distal movement of the tube 39 relative to the plunger 11, while permitting unlimited movement of the tube 39 in a proximal direction relative to the plunger.

The pair of telescoping guide tubes 38 and 39 form a conduit for the guidewire G, leading from the proximal end of the plunger to the entry throat of the housing 34 on the proximal end of the needle holder 14. Consequently, after the hypodermic needle 13 has punctured the patient's vein or artery, the user simply inserts the tip of the guidewire G into the open end of the guide tube 39 and manually advances the guidewire through the two guide tubes 39 and 38, the housing 34 and the two dome valves 35 and 36 therein, and on through the hollow needle 13 into the patient.

When the user desires to retract the hypodermic needle 13 within the barrel-plunger assembly, after the guidewire has been installed and the needle has been withdrawn from the patient and the guidewire, a mechanical latch 50 is manually actuated to unlock the arm 32. This permits rotation of the plunger 11 relative to the barrel 10, which in turn retracts and locks the needle-needle holder assembly within the barrel-plunger assembly. For the needle and needle holder to be moved to the retracted position, the plunger 11 can be in any desired position, e.g., to permit blood or medication to be retained in the syringe.

Figure 15:
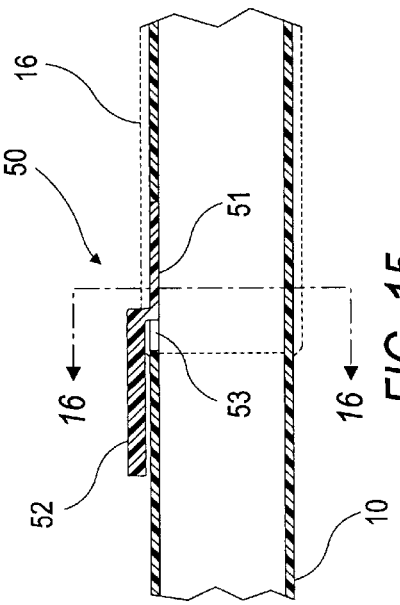
FIG. 15 is a fragmentary longitudinal section of the portion of the barrel of FIG. 14 that receives the latch mechanism.

The preferred latch mechanism 50 of FIGS. 1–5 includes an arcuate locking plate 51 and an integral handle 52 mounted for sliding movement within a short longitudinal slot 53 in the wall of the barrel 10. The free end of the plate 51 is angled to match the slope of the side walls of the spiral slot 19, and the plate slides back and forth within a slot 54 formed in the sleeve 16 and opening into the slot 19 adjacent the distal end of the slot. The inner and outer radii of the plate 51 match those of the sleeve 16 (see FIG. 2) to ensure that the locking plate 51 fits precisely into the slot 54 in the sleeve 16 and cannot fall inside the barrel cavity to obstruct movement of the plunger 11, in either the locked or unlocked position of the latch. As can be seen in FIG. 15, the locking plate 51 and the handle 52 are offset from each other in the radial direction so that the handle rides on the outer surface of the barrel 10. This outer handle surface is serrated to facilitate movement thereof with the user's finger or thumb.

The latch 50 can be opened or closed by linear movement of the locking plate 51 via the handle 52. During normal use, the needle holder arm 32 is positioned at the distal end of the spiral slot 19 and the locking plate 51 is advanced into the spiral slot 19 to close the slot and retain the arm 32 at the distal end of the slot 19. This locks the needle holder 14 in the normal operative mode in which only linear reciprocal movement of the plunger 11 is permitted. Because the locking plate 51 blocks the spiral slot 19, the needle holder 14 cannot rotate and thus cannot travel along the spiral slot 19 for retraction of the hypodermic needle 13. When it is desired to retract the needle, the latch handle 52 is retracted toward the distal end of the syringe, thereby opening the spiral slot 19 and permitting rotation of the plunger 11 and retraction of the needle holder 14 by movement of the arm 32 along the spiral slot.

It will be appreciated that when the latch 50 is retracted to open the spiral slot 19 and thereby unlock the arm 32, the plunger can be in any desired longitudinal position. That is, the plunger can be fully advanced, fully retracted, or at any intermediate position. This is advantageous because it might be desired to retain a portion of a blood sample withdrawn from a patient within the syringe. To prevent the leakage of any fluid contained within the syringe at the time the needle is retracted, it is preferred to provide a latex seal (not shown) at the end of the nozzle 15.

To ensure retention of the end portion of the arm 32 within the spiral slot 19 during retracting movement of the needle holder 14, the plunger 1, forms a solid cylinder interrupted only by the channel 33. The diameter of this cylinder matches the inside diameter of the barrel 10 so that it tends to maintain the desired circular shape of the inside wall of the barrel. Stresses exerted on the wall of the barrel during use can tend to distort the desired circular configuration of the barrel, and if the distortion becomes large enough, the arm 32 can escape from the spiral slot 19. With the solid cylindrical plunger riding on the inside wall of the sleeve 18, however, such excessive distortion is prevented, and thus retention of the arm 32 within the spiral slot 19 is ensured.

Figure 5:
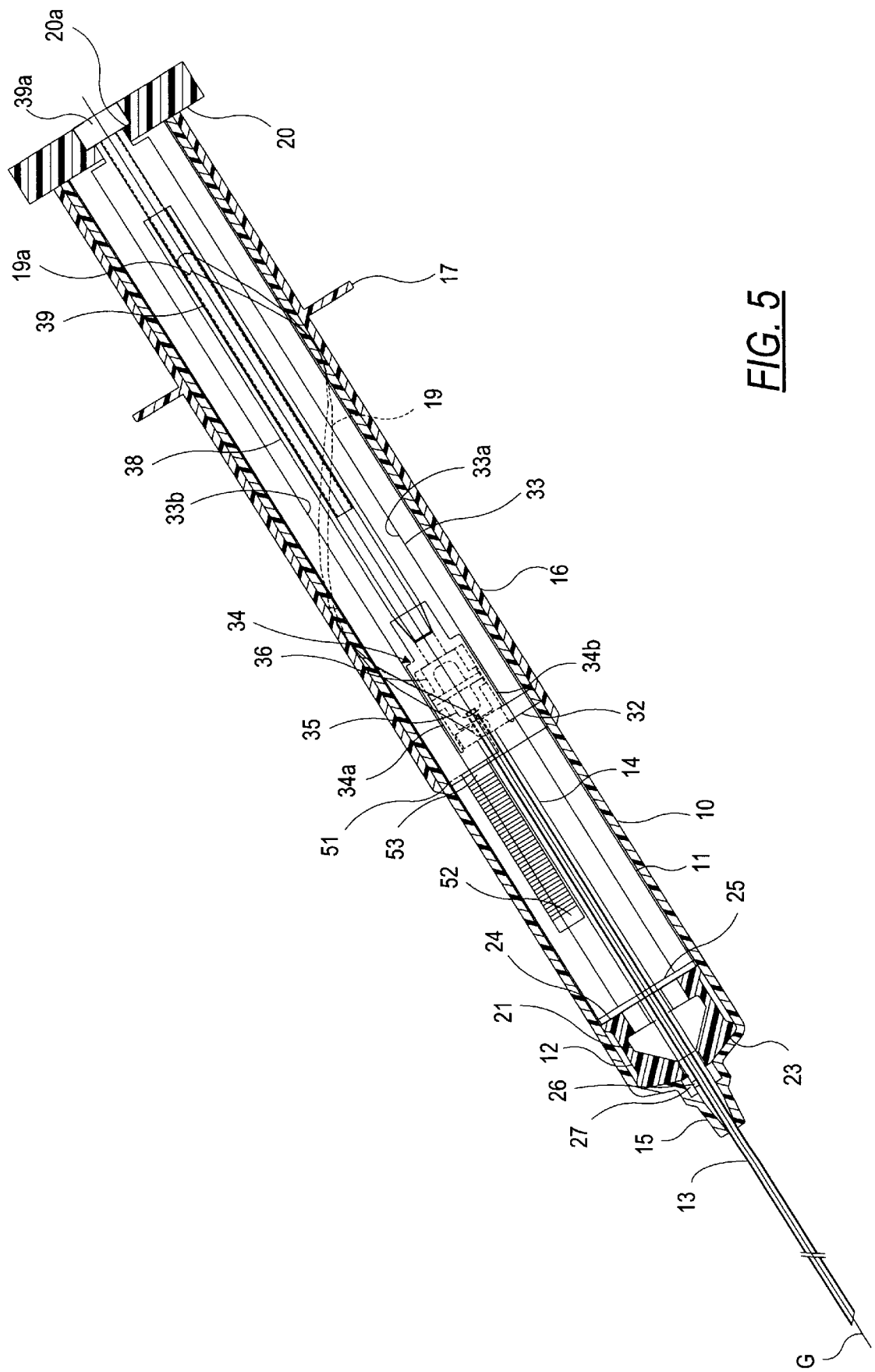
FIG. 5 is a longitudinal section of a needle-syringe-guidewire assembly embodying the present invention.
Figure 13:
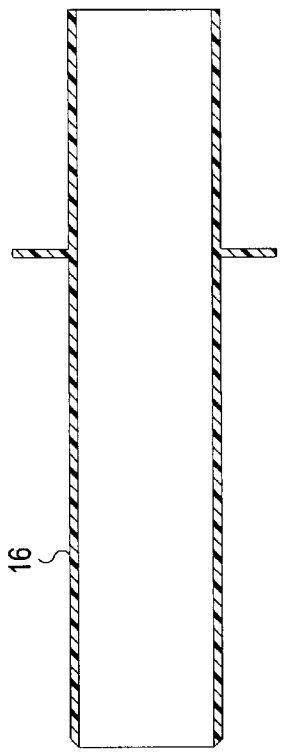
FIG. 13 is a longitudinal sectional view of the external sleeve in the assembly of FIGS. 1–8.
Figure 14:
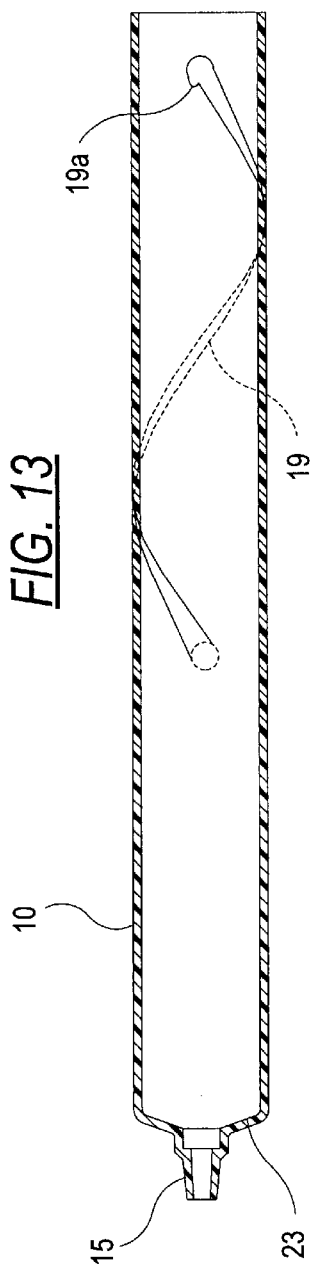
FIG. 14 is a longitudinal sectional view of the barrel in the assembly of FIGS. 1–8, with the portion of the spiral slot in the removed portion of the barrel shown in broken lines.
Figure 16:
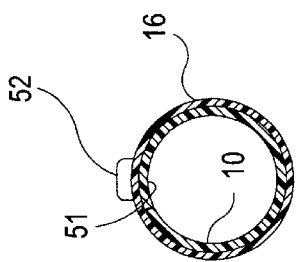
FIG. 16 is a section taken generally along line 16—16 in FIG. 15.

During normal use of the needle-syringe assembly, the barrel 10 and the needle holder 14 are held stationary, and the plunger 11 is free to move relative to both the barrel 10 and the needle holder 14. Advancing movement of the plunger 11 is limited by contact of the plunger cap 12 with the end wall of the barrel 10, as shown in FIGS. 5 and 6. Retracting movement of the plunger 11 is limited by contact of the plunger disc 25 with the arm 32, as shown in FIG. 7. If desired, stop members may be provided on the inside surface of the barrel to engage the disc 25 on the distal side of the latch opening, to further protect against the leakage of fluids through the latch opening in the barrel wall. The needle holder 14 is locked to the barrel 10 by virtue of the taper lock between the distal portion of the needle holder and the barrel nozzle 15, and the locking engagement of the lateral arm 32 in the wall of the barrel. Alternatively, the needle holder can be locked to the nozzle by a threaded connection, as described in more detail in the application Ser. No. 08/494,283 now U.S. Pat. No. 5,643,222. The plunger 11 is also free to move longitudinally relative to the needle holder 14, as illustrated in FIG. 7, because the needle holder is not locked to the plunger in that direction. The locking of the lateral arm 32 to the barrel wall prevents rotational movement of the plunger as well as the needle holder, and also prevents the plunger from being accidentally pulled out. As long as the lateral arm 32 of the needle holder is locked to the barrel wall, the needle-syringe assembly is in its normal operating mode.

Following insertion of the guidewire and removal of the needle from the patient, the needle 13 can be retracted into the plunger 11 and the barrel 10, as shown in FIG. 8. This requires axial movement of the needle holder 14 within the barrel 10 toward the proximal end thereof, which in turn requires that the needle holder 14 be unlocked for movement along the spiral slot 19. Thus, to initiate retraction of the needle holder 14, the arm 32 is unlocked by retracting the locking plate 51.

After the latching plate 51 has been retracted, the plunger knob 20 is turned to rotate the plunger 11 clockwise (as viewed from the proximal end) relative to the barrel. As the plunger is rotated, the needle holder 14 rotates in unison with the plunger because the arm 32 is fastened to the housing 34, which in turn is captured between the opposed parallel walls of the channel 32 in the plunger. Rotation of the needle holder 14 relative to the barrel 10 (1) retracts the needle holder within the plunger by the camming action of the wall of the spiral slot 19 acting on the arm 32, and (2) releases the locking luer taper at the distal end of the barrel nozzle 15 due to the resulting compound rotational and longitudinal forces applied to the tapered surfaces. As rotation continues, the arm 32 traverses the entire length of the spiral slot 19, thereby retracting the entire needle holder 14 through a corresponding axial distance within the plunger 11 (see FIG. 8). Of course, the needle 13 is retracted along with the needle holder 14, and thus the needle is retracted completely within the barrel nozzle 10 and the plunger 11, as illustrated in FIG. 8.

As an alternative to the illustrative embodiment, the spiral slot 19 may be formed in a sleeve fitted inside an enlarged distal end portion of the barrel 10, and attached to the barrel. The spiral slot preferably has a constant rate of curvature along its length. The portion of the barrel 10 that receives the sleeve has a slightly larger diameter than the central portion of the barrel, and the sleeve has the same inside diameter as the central portion of the barrel. Alternatively, a spiral channel can be molded as a part of the inside wall of the end portion of the barrel that has the slightly larger diameter.

At the distal end of the spiral slot 19, the end of the arm 32 snaps into a detent notch 19a formed by the walls of the slot so that the user feels the end of the needle retraction, as a click. Then if the user attempts to turn the plunger knob 20 in the opposite direction, such attempt is met with firm resistance. This is a safety feature to prevent the needle from being returned beyond the end of the barrel nozzle, and to discourage re-use of the needle.

To operate the guidewire-syringe the area of the intended procedure is scrubbed, cleaned and draped, the intended vein or artery is localized by anatomical landmarks and the area is locally anesthetized. After removing the protective cap, the guidewire-syringe is primed with normal saline to remove traces of air. The intended vessel is then punctured and access is confirmed by aspiration of the blood in the syringe. After confirming the vessel entry the aspirated blood is returned to the patient. The straightened guidewire is then fed into the opening at the face plate of the plunger. The guidewire passes through the valve, the needle holder and the hypodermic needle into the patient's vein/artery. Once a required length is introduced, the syringe is withdrawn, leaving the guidewire in place. This leaves the guidewire exiting from the patient's skin in a blood-less environment. The latch handle 52 is then retracted to open the spiral channel 19, and the plunger knob 20 is rotated clockwise until the user feels the arm 32 snap into the detent notch 19a at the proximal end of the spiral slot 19. The spiral slot 19 may alternatively be configured to require counterclockwise, instead of clockwise, rotation of the plunger knob 20. With the needle 13 completely retracted inside the barrel 10, the needle-syringe assembly can be safely discarded in its entirety.

It can be seen from the foregoing description that the needle-syringe-guidewire assembly performs all the conventional functions of guidewire introducers and yet, upon completion of the guidwire installation, the hypodermic needle 13 is concealed within the barrel 10. Another advantage of the needle-syringe assembly is that its design prevents the plunger 11 from slipping out of the barrel 10 during normal use of the assembly.

The needle-syringe-guidewire assembly of this invention is easy to manufacture, cost-effective, and easy to use in the field. The parts can all be made by conventional plastic molding and using readily available metal needle stock. The plastic parts can be made by injection molding medical grade polymers such as polypropylene. The plunger seal or cap can be molded from natural or synthetic elastomeric polymers. The guide sleeve with the spiral slot can be molded and press fit into the wide end of the barrel. The spiral channel on the inside wall of the barrel can be molded with rotating cores which are removed by rotating them while withdrawing them from the molded part.

The final assembly is compact because the needle holder 14 is retracted directly into the plunger 11 itself, and thus the plunger 11 need not be fully extended for needle retraction to occur. When discarded following use, the needle-syringe assembly contributes minimally to the bulk of refuse. Since retraction of the needle 13 is effected by turning the plunger knob 20 at the proximal end of the assembly, the hand of a user does not come into the vicinity of the needle point, thereby minimizing the possibility of a needle prick during retraction. Moreover, the assembly employs substantially the same number of components as conventional syringes, and does not require additional guards, sheaths, sleeves, springs, etc. to conceal the needle following use.

If desired, the spiral slot 19 may be integrally molded on the inner surface of a proximal end portion of the barrel 10 having an increased wall thickness. Internal molding of the spiral slot is possible when mold cores are rotated while they are pulled from the mold cavity used to form the barrel. A latch mechanism may be mounted in a straight longitudinal slot that opens through the proximal end of the barrel and continues as a straight longitudinal channel on the inside wall of the barrel. The spiral slot preferably extends less than 360 degrees around the circumference of the barrel, and opens through the proximal end of the barrel. This avoids interference between the spiral slot and the latch channel.

The illustrative spiral slot, which extends through the entire thickness of the barrel wall, is preferred because it facilitates molding of the barrel, including the spiral slot, without the use of any special technique. The position of the finger flange and the length of the barrel extension on the proximal side of the flange can be varied as required to retract needles of different lengths.

A modified latch arrangement is illustrated in FIGS. 23–25. In this design the spiral slot 19 extends through the wall of the barrel, and a smooth sleeve 40 is telescoped over the proximal end portion of the barrel to cover the slot. The distal end portion 41 of the sleeve 40 is enlarged and has an oval or elliptical transverse cross-section. The minor axis of the ellipse extends over the distal end of the spiral slot 19, and inwardly projecting lug 42 on the inside surface of the sleeve portion 41 of the minor axis extends into the distal end of the slot, on the proximal side of the arm 32. This forms a latch that holds the arm 32 against the distal end of the slot 19. The opposite side of the elliptical end portion 41 is permanently bonded to the outer surface of the barrel 10 by various means such as ultrasonic bonding. When it is desired to release the latch, the user presses on opposite ends of the major axis of the ellipse, thereby converting the elliptical cross-section to a generally circular cross-section. As illustrated by the broken-line illustration in FIG. 25, this deformation causes the lug 42 to be withdrawn from the slot 19, thereby unlatching the arm 32 so that it can be moved along the spiral slot 19. When the deforming pressure is released from the sleeve portion 41, the memory of the resilient plastic material of the sleeve 40 causes the end portion 41 to return to its normal elliptical shape, and the lug 42 re-enters the spiral slot 19.

I claim:

1. A needle-syringe assembly for inserting a guidewire in a patient, comprising:

an elongated, generally cylindrical barrel forming a hollow nozzle located at the distal end of said barrel and opening into the interior of said barrel;

a plunger slidably mounted in said barrel and forming a longitudinal cavity;

a hollow needle holder slidably mounted in said longitudinal cavity of said plunger;

hollow guide means mounted between the proximal ends of said needle holder and said plunger for guiding a guidewire from the proximal end of said plunger to the proximal end of said needle holder, said needle holder including valve means for passing a guidewire therethrough while preventing blood from flowing between the interiors of said needle holder and said hollow guide means, guide means forming a spiral channel extending along a proximal end portion of said barrel for engaging a lateral extension of said needle holder and retracting said needle holder within the barrel in response to relative rotational movement between the barrel and the needle holder, said lateral extension extending from said longitudinal cavity; and latching means on said barrel for latching and unlatching said lateral extension of said needle holder at the distal end of said spiral channel.

2. The needle-syringe assembly of claim 1 wherein said hollow guide means comprises first and second of telescoping tubular members extending between the proximal ends of said needle holder and said plunger to permit relative longitudinal movement between said needle holder and plunger, the distal end of said first tubular member being attached to said needle holder, and the proximal end of said second tubular member extending through the proximal end of said plunger.

3. The needle-syringe assembly of claim 2 wherein said second tubular member includes means for preventing the proximal end of said second tubular member from moving inside the plunger.

4. The needle-syringe assembly of claim 2 wherein the proximal end of said plunger forms an opening into the interior of said telescoping tubular members for permitting the insertion of a guidewire into said tubular members.

5. The needle-syringe assembly of claim 2 wherein the interior of said telescoping tubular members is longitudinally aligned with, and in communication with, the interior of said needle holder.

6. The needle-syringe assembly of claim 1 wherein said plunger includes contacting means extending transversely across the interior of said barrel and sliding along the interior surface of said guide means that forms said spiral channel so as to maintain the desired configuration of that surface and thereby ensure engagement of said needle holder with said spiral channel.

7. The needle-syringe assembly of claim 6 wherein said contacting means includes a circular plate formed as an integral part of said plunger.

8. The needle-syringe assembly of claim 6 wherein said contacting means also includes a plurality of longitudinal elements formed as integral parts of said plunger and sliding along the interior surface of said guide means to maintain the desired configuration of that surface.

9. The needle-syringe assembly of claim 1 wherein said latching means comprises a blocking element slidably mounted on said barrel for reciprocating movement between a blocking position within said spiral channel and a non-blocking position outside said spiral channel.

10. The needle-syringe assembly of claim 9 wherein said latching means includes a manually actuatable handle attached to said blocking element and exposed on the outer surface of said barrel for effecting sliding movement of said blocking element.

11. The needle-syringe assembly of claim 1 wherein said spiral channel is formed in the wall of said barrel and extends radially through the wall of said barrel.

12. The needle-syringe assembly of claim 11 which includes an outer sleeve telescoped over said barrel and covering at least a distal end portion of said spiral channel.

13. The needle-syringe assembly of claim 1 wherein said spiral channel includes means at the proximal end thereof for resisting advancing movement of said needle holder after it has been fully retracted.

14. The needle-syringe assembly of claim 13 wherein said means at the proximal end of said spiral channel is a detent.

15. The needle-syringe assembly of claim 1 wherein said valve means comprises a pair of oppositely facing dome valves.

16. The needle-syringe assembly of claim 1 wherein said lateral extension includes a lateral arm extending laterally through said plunger cavity to said barrel, and said latching means is mounted for movement in and out of said spiral channel for capturing and releasing said needle holder arm at the distal end of said spiral channel.

17. The needle-syringe assembly of claim 1 wherein said latching means is slidably mounted in a slot formed in said barrel and opening into said spiral channel at one end of the channel.

18. The needle-syringe assembly of claim 1 which includes a hollow needle attached to the distal end of said needle holder.

19. The needle-syringe assembly of claim 1 wherein said latching means includes a slidable plate which forms a distal end portion of a side wall of said spiral channel when said plate is in a retracted (open) position, and which blocks said channel and captures said needle holder at the distal end of said channel when said plate is in an advanced (closed) position.

20. A needle-syringe assembly, comprising:
an elongated, generally cylindrical barrel forming a hollow nozzle located at the distal end of said barrel and opening into the interior of said barrel;
a plunger slidably mounted in said barrel and forming a longitudinal cavity;
a needle holder slidably mounted in said longitudinal cavity of said plunger;
hollow guide means mounted between the proximal ends of said needle holder and said plunger for guiding a guidewire from the proximal ends of said plunger to the proximal end of said needle holder,
said needle holder including valve means for passing a guidewire therethrough while preventing blood from flowing between the interiors of said needle holder and said hollow guide means,
said barrel forming a spiral channel extending along a proximal end portion of said barrel for engaging a lateral extension of said needle holder and retracting said needle holder within the barrel in response to relative rotational movement between the barrel and the needle holder, said lateral extension extending from said longitudinal cavity. said spiral channel extending through the wall of said barrel.

21. The needle-syringe assembly of claim 20 which includes latching means movably mounted on said barrel for movement into and out of engagement with said lateral extension of said needle holder for latching and unlatching said needle holder at the distal end of said spiral channel.

22. The needle-syringe assembly of claim 21 wherein said latching means is slidably mounted in a slot formed in said barrel and opening into said spiral channel at one end.

23. The needle-syringe assembly of claim 20 wherein said latching means comprises a blocking element slidably mounted on said barrel for reciprocating movement between a blocking position within said spiral channel and a non-blocking position outside said spiral channel.

24. The needle-syringe assembly of claim 23 wherein said latching means includes a manually actuatable handle attached to said blocking element and exposed on the outer surface of said barrel for effecting sliding movement of said blocking element.

25. The needle-syringe assembly of claim 23 wherein said contacting means includes a circular plate formed as an integral part of said plunger.

26. The needle-syringe assembly of claim 25 wherein said contacting means also includes a plurality of longitudinal elements formed as integral parts of said plunger and sliding along the interior surface of said guide means to maintain the desired configuration of that surface.

27. The needle-syringe assembly of claim 20 which includes a solid sleeve telescoped over said barrel and attached thereto, said sleeve covering at least a distal portion of said spiral channel.

28. The needle-syringe assembly of claim 20 wherein said lateral extension includes a lateral arm extending laterally through said plunger cavity to said barrel, and which includes latching means mounted for movement in and out of said spiral channel for capturing and releasing said needle holder arm at the distal end of said spiral channel.

29. The needle-syringe assembly of claim 20 which includes a hollow needle attached to the distal end of said needle holder.

30. The needle-syringe assembly of claim 20 wherein said plunger includes contacting means extending transversely across the interior of said barrel and sliding along the interior surface of said guide means that forms said spiral channel so as to maintain the desired configuration of that surface and thereby ensure engagement of said needle holder with said spiral channel.

31. A needle-syringe assembly for inserting a guidewire in a patient, comprising
a barrel, a plunger within the barrel for sliding longitudinal movement and rotational movement relative to the barrel, and a hollow needle holder within the plunger for sliding longitudinal movement relative to the plunger, said needle holder being moveable beyond the distal end of said plunger for advancing a needle through and beyond the distal end of said barrel,
sealing means at the distal end of the needle holder for sealing the interface between the barrel and the needle holder against fluid flow when the needle holder is in its most distal position, hollow guide means mounted between the proximal ends of said needle holder and said plunger for guiding a guidewire from the proximal ends of said plunger to the proximal end of said needle holder, said needle holder including valve means for passing a guidewire therethrough while preventing blood from flowing between the interiors of said needle holder and said hollow guide means, means for retracting said needle holder relative to said barrel in response to relative rotational movement between the plunger and the barrel, and latch means for selectively locking said needle holder to said barrel to prevent relative rotational movement therebetween.

32. A needle-syringe assembly for inserting a guidewire in a patient, comprising:

an elongated, generally cylindrical barrel forming a hollow nozzle located at the distal end of said barrel and opening into the interior of said barrel;

a plunger slidably mounted in said barrel and forming a longitudinal cavity;

a hollow needle holder slidably mounted in said longitudinal cavity of said plunger;

hollow guide means mounted between the proximal ends of said needle holder and said plunger for guiding a guidewire from the proximal end of said plunger to the proximal end of said needle holder, said needle holder including valve means for passing a guidewire therethrough while preventing blood from flowing between the interiors of said needle holder and said hollow guide means, guide means forming a spiral channel extending along a proximal end portion of said barrel, a portion of said needle holder extending laterally into said channel for retracting said needle holder within the barrel in response to relative rotational movement between the barrel and the needle holder; and latching means movably mounted on said barrel for movement into and out of engagement with said portion of said needle holder that extends laterally into said channel for latching and unlatching said needle holder at the distal end of said spiral channel.

33. A needle-syringe assembly, comprising:

an elongated, generally cylindrical barrel forming a hollow nozzle located at the distal end of said barrel and opening into the interior of said barrel;

a plunger slidably mounted in said barrel and forming a longitudinal cavity;

a needle holder slidably mounted in said longitudinal cavity of said plunger;

hollow guide means mounted between the proximal ends of said needle holder and said plunger for guiding a guidewire from the proximal end of said plunger to the proximal end of said needle holder, said needle holder including valve means for passing a guidewire therethrough while preventing blood from flowing between the interiors of said needle holder and said hollow guide means, said barrel forming a spiral channel extending along a proximal end portion of said barrel, a portion of said needle holder extending laterally into said channel for retracting said needle holder within the barrel in response to relative rotational movement between the barrel and the needle holder, said spiral channel extending through the wall of said barrel.

* * * * *

UNITED STATES PATENT AND TRADEMARK OFFICE
CERTIFICATE OF CORRECTION

PATENT NO.: 5,879,338
DATED: March 9, 1999
INVENTOR(S): Mahurkar

It is certified that errors appear in the above-identified patent, and that said Letters Patent is hereby corrected as shown below.

Column 12, Claim 25, line 27, delete "claim 23" and insert --claim 30--

Signed and Sealed this

Twenty-seventh Day of July, 1999

*Attest:*

Q. TODD DICKINSON

*Attesting Officer*      Acting Commissioner of Patents and Trademarks